US005619372A

United States Patent [19]
Hellmuth et al.

[11] Patent Number: 5,619,372
[45] Date of Patent: Apr. 8, 1997

[54] STEREOMICROSCOPE FOR MAKING TRANSPARENT MEDIA VISIBLE AND METHOD THEREFOR

[75] Inventors: Thomas Hellmuth, Danville, Calif.; Peter Seidel, Steinheim; Peter Schäffer, Oberkochen, both of Germany

[73] Assignee: Carl-Zeiss-Stiftung, Heidenheim, Germany

[21] Appl. No.: 288,305

[22] Filed: Aug. 10, 1994

[30] Foreign Application Priority Data

Aug. 10, 1993 [DE] Germany .......................... 43 26 761.0

[51] Int. Cl.$^6$ .............................. G02B 21/06; G02B 21/00
[52] U.S. Cl. ........................ 359/389; 359/368; 359/370; 359/385
[58] Field of Search .................................. 359/368–371, 359/379–380, 385–389, 232–235; 351/214, 221, 243

[56] References Cited

U.S. PATENT DOCUMENTS

| | | | |
|---|---|---|---|
| 2,553,108 | 5/1951 | Osterberg et al. | 359/370 |
| 2,660,923 | 12/1953 | Benford | 359/370 |
| 2,977,847 | 4/1961 | Meyer-Arendt | 359/370 |
| 4,265,518 | 5/1981 | Matsumura | 351/215 |
| 4,407,569 | 10/1983 | Piller et al. | 359/370 |
| 5,126,877 | 6/1992 | Biber | 359/389 |
| 5,446,509 | 8/1995 | Okinishi | 351/214 |

Primary Examiner—Thong Nguyen
Attorney, Agent, or Firm—Walter Ottesen

[57] ABSTRACT

Phase-contrasting elements are arranged in the viewing beam paths of a stereomicroscope to make transparent media visible with rich contrast such as in the area of ophthalmologic surgery. The phase-contrasting elements make the transparent media visible as phase objects in the amplitude contrast. The phase-contrasting elements are selected in dependence upon the light source diaphragm which is used.

18 Claims, 5 Drawing Sheets

STEREOMICROSCOPE FOR MAKING TRANSPARENT MEDIA VISIBLE AND METHOD THEREFOR

FIELD OF THE INVENTION

The invention relates to a stereomicroscope such as a stereomicroscope for ophthalmologic surgery. The stereomicroscope of the invention makes transparent mediums visible so that they are rich in contrast. The invention is also directed to a method of operating a stereomicroscope of this kind.

BACKGROUND OF THE INVENTION

A stereomicroscope is conventionally used in microsurgical procedures on the eye. The so-called red-reflex illumination is utilized in the stereomicroscope in order to ensure a reliable and complete removal of the clouded eye lens in cataract surgery. Here, the ocular fundus diffusely reflects the incident illuminating light. The forward transparent sections of the eye appear in red transmitted light for the operating surgeon because of the absorption characteristics of the retina. Illuminating conditions of this kind are characterized in the following as "reflected transmitted light".

After drawing off the clouded eye lens with a so-called phaco-emulsificator, it is important for the operating surgeon to detect transparent lens residues, which may possibly still remain, in the forward eye section in order to likewise completely remove the same.

Up to now, efforts were made for the most part to intervene at the illuminating side in the stereomicroscope so that a red reflex resulted which was as homogeneous as possible in order to be able to clearly perceive lens residues in the forward section of the eye. In this connection, reference may be made to U.S. Pat. No. 5,126,877.

However, these interventions in the illuminating beam path of the particular stereomicroscope used did not always provide an adequate contrast of the substantially transparent media of the forward eye section.

SUMMARY OF THE INVENTION

It is an object of the invention to provide a stereomicroscope especially a stereomicroscope for ophthalmologic surgery and a method to operate the same which provides a good contrast of the transparent media in the transmitted light.

According to the invention, the transparent media are viewed in the transmitted light as phase objects which are imaged with amplitude contrast or made visible by suitable phase contrasting elements in the stereomicroscope. For this purpose, and according to the invention, intervention is carried out at a location in the viewing beam path of the stereomicroscope where the diffraction images of the light source are located. There, by means of suitable phase-contrasting elements, one can selectively mask out specific diffraction orders from the diffraction patterns without great effort or shift the specific diffraction orders in their phases relative to each other. This location lies in the ocular fundus image plane of the stereomicroscope or close thereto during use in cataract surgery because of the geometric imaging conditions.

In this application for the stereomicroscope according to the invention, an imaging of the primary light source image takes place via the illumination beam path in a primary light source image plane which is coincident with the ocular fundus of the eye being viewed. The primary light source image on the ocular fundus is imaged in a secondary light source image plane via the eye lens, cornea and viewing optic of the stereomicroscope. The secondary light source image plane then corresponds to the ocular fundus image plane. In this plane, the phase contrasting elements are arranged according to the invention in the viewing beam paths. With these measures, interferences result between the diffraction orders, which were not masked, of the waves diffracted at the phase objects and the waves of zero order diffraction, which pass through the phase objects, so that amplitude images become visible for the viewer.

When used in ophthalmologic surgery, the stereomicroscope according to the invention ensures that the transparent media in the forward eye section are made visible with rich contrast. Safe work for the operating surgeon is possible.

In addition to ophthalmologic surgery, the stereomicroscope of the invention can be advantageously utilized everywhere where light transparent objects are to be made visible with rich contrast in reflected transmitted light.

In the stereomicroscope according to the invention, intervention takes place in the illuminating beam path by means of a suitable light source diaphragm in such a manner that a point or slit-shaped primary light source image is imaged. The slit-shaped primary light source image can be configured to be rectangular or ring-shaped. The particular phase-contrasting elements are then selected in dependence upon the form of the primary light source image.

When utilizing the stereomicroscope of the invention in ophthalmologic surgery, the particular primary light source image lies in the ocular fundus plane and the transparent media in the forward section of the eye are transilluminated by the light reflected at the ocular fundus.

The illumination described to this point is illumination in the reflected transmitted light. According to the invention, an illumination arrangement is possible wherein the transparent parts of the forward section of the eye are transilluminated from the rear by a fiber-optic light conductor placed intraocularly. In this way, a transillumination of these sections of the eye is provided.

The required measures for improving contrast of the transparent media can be carried out without much adjusting effort, that is, especially the arrangement of suitable phase-contrasting elements in the stereomicroscope. The phase-contrasting elements as well as the elements in the illuminating beam path for dimensioning the light source image can, in addition, be mounted so as to be selectively pivoted in and pivoted out. In this way, the stereomicroscope of the invention can, for example, also be used in other disciplines within microsurgery at any time.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
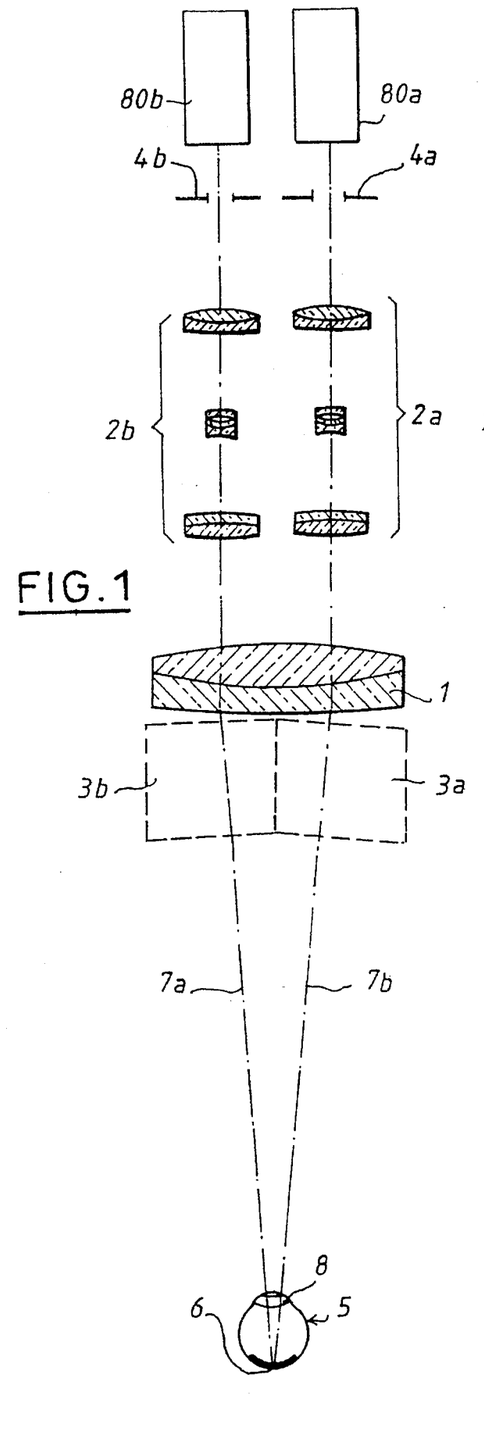
FIG. 1 is a schematic representation of a front elevation view of the stereomicroscope according to the invention with the two viewing beam paths as well as the arrangement of the phase-contrasting elements including the imaging conditions in the ophthalmologic surgery also in schematic representation.

FIG. 1 shows a front view of a stereomicroscope with the phase-contrasting elements mounted therein for use in ophthalmologic surgery. The stereomicroscope per se shown in FIG. 1 is of known configuration. The microscope includes a one-piece main objective 1 for both viewing beam paths, that is, the main objective is configured pursuant to the so-called telescope principle. The optical axes (7a, 7b) for the two viewing beam paths, respectively, are shown in FIG. 1.

The features of the invention can also be applied in a stereomicroscope for which a separate objective is provided for each viewing beam path, that is, in a stereomicroscope pursuant to the Greenough principle.

A magnification-changing device (2a, 2b) is mounted downstream of the common main objective 1. This magnification-changing device is configured here as a Galilei changer. Alternatively, a zoom system can be utilized at any time which permits a continuous variation of the actual magnification. The magnification-changing device (2a, 2b) can also be mounted after out-coupling and in-coupling elements in the two viewing beam paths. These elements are not shown in FIG. 1 for reasons of clarity. These elements operate to couple in intermediate images into the viewing beam path or to couple out the viewing beam paths to CCD cameras and the like for documentation purposes.

In the embodiment shown, phase-contrasting elements (4a, 4b) are fixedly arranged in the two viewing beam paths in the ocular fundus image plane or the secondary light source image plane of the stereomicroscope. The following are arranged after the phase-contrasting elements (4a, 4b): a binocular tube having tube lenses, deflecting prisms and ocular lenses which, for reasons of clarity, is represented schematically by block 80a and 80b in FIG. 1. A binocular tube of this kind is shown in U.S. Pat. No. 4,175,836 incorporated herein by reference.

Deflecting elements (3a, 3b) are mounted below the main objective 1 and deflect the illuminating beam path in the direction of the eye 5 to be operated. The illuminating beam path is not shown in FIG. 1.

Alternatively, it is also possible to couple in the illuminating beam path above the main objective 1 via suitably mounted deflecting elements.

In the configuration of the invention of the stereomicroscope for ophthalmologic surgery, the premise is taken that a primary light source image is formed on the ocular fundus 6 with this primary light source image approximating a point or a slit. Various slit forms are possible which will be explained in greater detail hereinafter.

The media of the forward section 8 of the eye are transilluminated by a wave emanating from or reflected by the fundus 6. The starting point of this wave is defined by the particular primary light source image on the ocular fundus 6. The transparent objects in the forward section 8 of the eye such as lens residues or the like effect a phase shift of the wave trains which transilluminate these lens residues. However, this is not adequate to make these phase objects visible for the viewer without additional measures. The human eye cannot perceive the location of phase differences; instead, the resulting phase difference must be translated into an amplitude contrast after transillumination of the forward section of the eye. The diffraction orders of the waves diffracted at the phase object are clearly present separate from each other in the secondary light source image plane in the viewing beam path.

According to the invention, if one intervenes in the secondary light source image plane in the viewing beam path, then it is possible to image the transparent objects in the forward section 8 of the eye with amplitude contrast. For this purpose, one of the higher orders (such as the +1 or −1 diffraction order) is masked out with the aid of a suitable phase-contrasting element (4a, 4b). The remaining diffraction orders interfere with the zero diffraction order, that is the undiffracted transmitted wave, and effect an amplitude contrast in this way. Accordingly, steps must be taken, with suitable phase-contrasting elements that the phase-shifted diffracted wave components interfere with the non-diffracted wave component so that amplitude contrast occurs. A detailed explanation as to various embodiments of suitable phase-contrasting elements (4a, 4b) will be provided with respect to FIGS. 3a to 3c.

The ocular fundus image plane has been shown to be a suitable plane for arranging the phase-contrasting elements (4a, 4b). In the above-described illuminating arrangement, the ocular fundus image plane is identical to the secondary light source image plane of the idealized light source on the ocular fundus 6. In the illustrated embodiment, the ocular fundus image plane lies between the magnification-changing device (2a, 2b) and the binocular tubes 80a and 80b. The fundus image plane or the light source image plane can assume a different position along the optical axes (7a, 7b) of the viewing beam paths in dependence upon the adjusted magnification. For this reason and according to the invention, it is also possible in a stereomicroscope of variable magnification, to couple the position of the phase-contrasting elements (4a, 4b) to the particular adjusted magnification of the magnification-changing device (2a, 2b). Depending upon actual magnification, the phase-contrasting elements provided in each case are shifted along the optical axes (7a, 7b) in the viewing beam paths into the secondary light source image plane. The position of the secondary light source image plane is known based on the optical data of the stereomicroscope as is the main objective focal distance and the particular magnification which has been set.

A coupling between actually adjusted magnification and position of the phase-contrasting elements along the optical axes can be realized via a mechanical coupling in the form of a gear drive.

Alternatively, a closed-loop control circuit can be utilized wherein the particular actual magnification can be detected with the aid of a suitable detector such as an encoder on the operator-controlled element of the magnification-changing device. Here, the detector signal functions as a control variable for a drive. The phase-contrasting elements are shifted in the viewing beam paths along the optical axis within a specific path interval via the drive and are, in this way, positioned in the secondary light source image plane.

Figure 5:
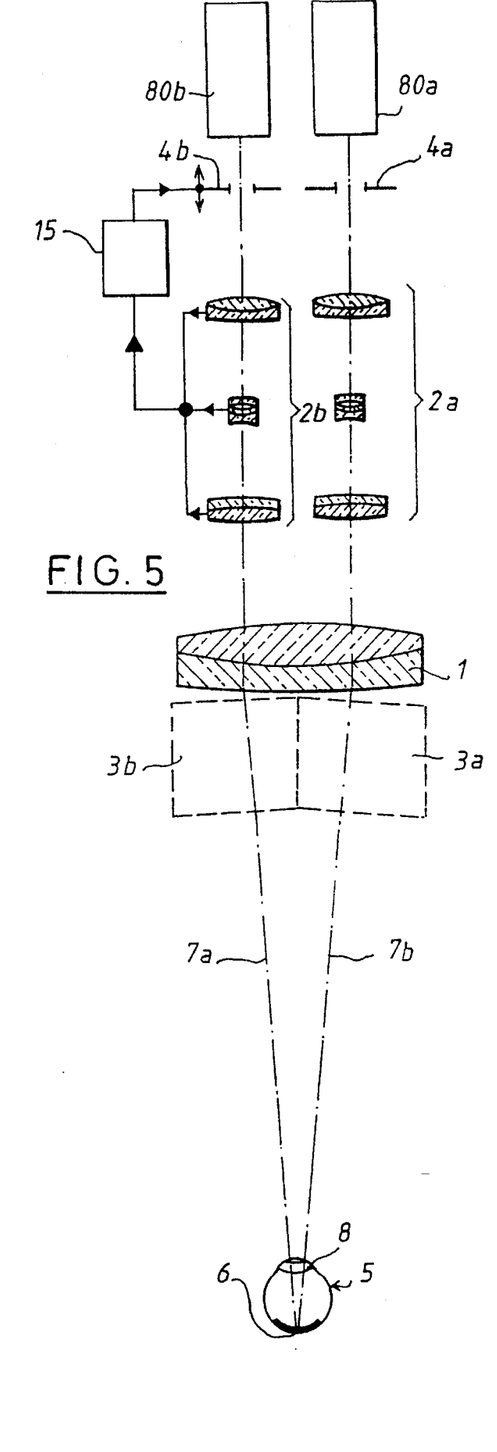
FIG. 5 is a schematic representation of a front elevation view of the stereomicroscope according to another embodiment of the invention showing a coupling between the magnification setting and the position of the phase-contrasting elements in the stereoscopic beam paths.

A coupling is shown in FIG. 5 between the actual adjusted magnification of the stereomicroscope and the position of the phase-contrasting elements along the optical axes. The coupling device 15 detects the actual magnification of the magnification changing device (2a, 2b) and utilizes this data to correspondingly position the phase-contrasting elements along the optical axes. The coupling 15 must be provided for both stereoscopic viewing beam paths. For reasons of clarity, FIG. 5 shows only the coupling device 15 for one of the two stereoscopic viewing beam paths.

Figure 2:
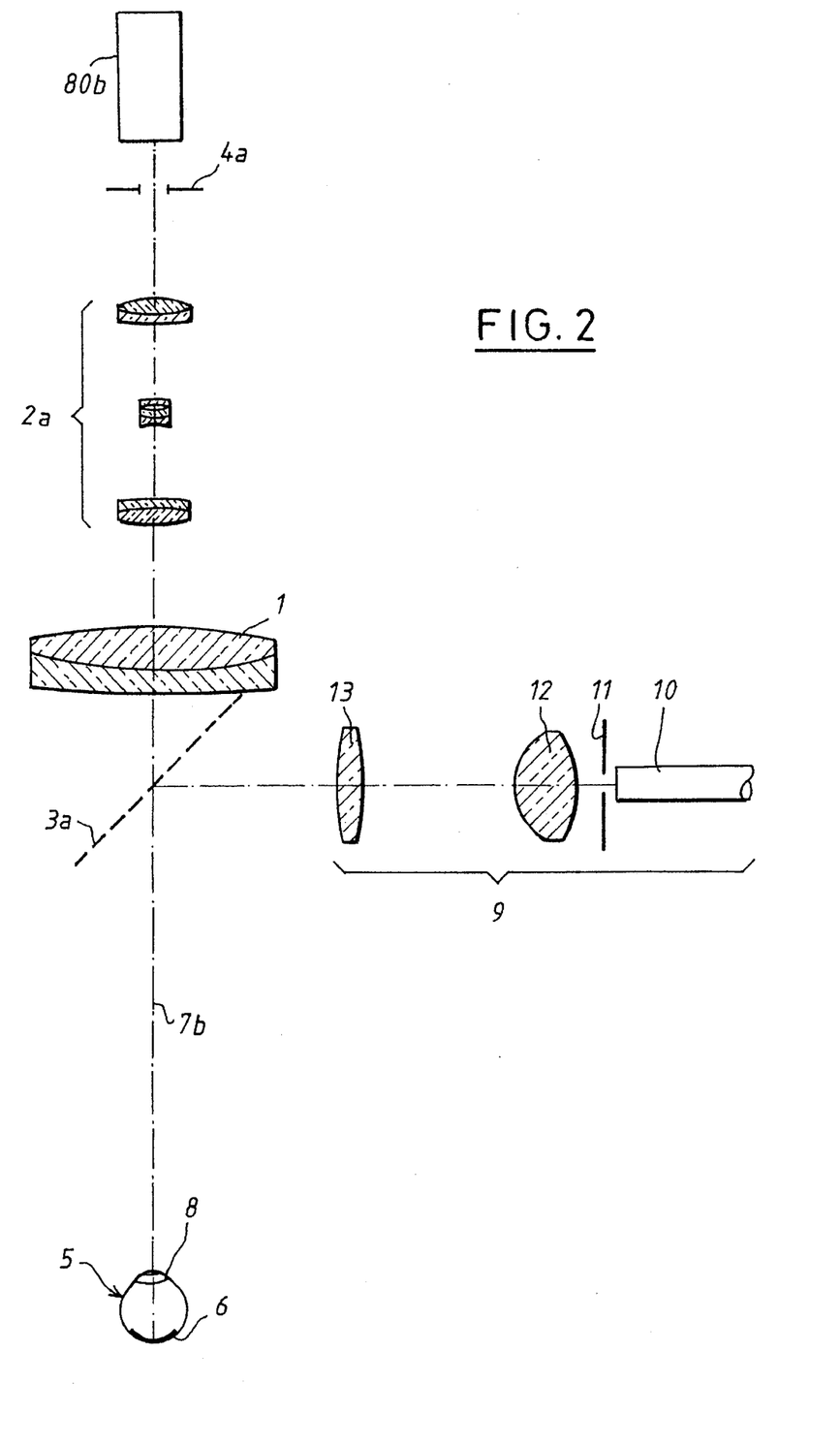
FIG. 2 is a side elevation view of the stereomicroscope arrangement of FIG. 1 including the arrangement of the illuminating beam path.

In FIG. 2, the stereomicroscope of the invention is shown in a side elevation view including the sketched imaging conditions in the ophthalmologic surgery shown in FIG. 1. Identical elements are here identified by the same reference numerals as in FIG. 1.

In FIG. 2, the illuminating beam path 9 is clearly seen orientated at a 90° angle to the plane of the two viewing beam paths. In the embodiment shown, the illuminating beam path 9 includes a fiber-optic light conductor 10 having a downstream light source diaphragm 11 as well as a two-part imaging optic (12, 13). The light source diaphragm 11 in the illuminating beam path acts to dimension the form and/or size of the desired light source image on the ocular fundus 6. The light source diaphragm 11 used can be mounted directly forward of the outlet surface of the fiber-optic light conductor 10 as shown in FIG. 2. Alternatively, it is possible to arrange the light source diaphragm 11 at a specific distance forward of the outlet surface of the fiber-optic light conductor 10 and to image the outlet surface in the light source diaphragm 11 by means of a suitable imaging optic.

Likewise, it is possible to select the outlet surface of the fiber-optic light conductor in the required form. For this purpose, the otherwise necessary light source diaphragm is unnecessary and no losses result when masking out unwanted components of the beam cross section.

Other light sources such as cold light mirror lamps or the like can be used in lieu of the fiber-optic light conductor.

Depending upon requirements or purpose of utilization, the diaphragm 11 used has a different form and/or size. The light source diaphragm 11 can, for example, be slit-shaped, point-shaped, annularly-shaped or circularly-shaped as will be explained in greater detail with respect to FIGS. 4a to 4c.

The illuminating beam path 9 is deflected in the direction of the eye 5 to be viewed via the deflecting mirror 3a or another suitable deflecting element. The selection of a suitable deflecting element is made in dependence upon the desired light source image.

For a desired point-shaped or circularly-shaped light source image, it must be ensured that the light source image is imaged in the ocular fundus image plane concentric to the optical axis of the particular viewing beam path. This is ensured by means of the suitable configuration of the illuminating beam path. This can, for example, be realized either by two completely separate illuminating beam paths or by splitting one single illuminating beam path into two component illuminating beam paths.

A conventional one-piece deflecting mirror can be used for a slit-shaped light source image which extends along the connecting line of the optical axes of the viewing beam paths.

The imaging optic (12, 13) in the illuminating beam path 9 can (for optimal adaptation of the illuminating conditions to the particular use conditions) be so configured that a variable focusing of the light source image by the user is possible by means of a linearly displaceable optical element within the imaging optic (12, 13). For use of the stereomicroscope of the invention in the context of ophthalmologic surgery, an adaptation to different patient eyes is possible in that, via the focusing capability in the illuminating beam path 9, it is ensured that a sharp light source image is imaged on the ocular fundus 6 of the eye 5 to be viewed.

In addition to the single component illuminating beam path already shown with an individual light source, it is also possible to utilize two separate light sources and to image suitable light source image diaphragms in the first light source image plane via two component illuminating beam paths. Correspondingly, a suitable deflection of these component illuminating beam paths must be provided.

The phase-contrasting element 4a of the left viewing beam path can be seen in FIG. 2 between the magnification-changing device 2a and the binocular tube 80a. The corresponding phase-contrasting element in the second viewing beam path lies therebehind and is not shown.

In addition to the fixed arrangement of the phase-contrasting elements in the viewing beam paths, it is possible in a further embodiment of the stereomicroscope of the invention to mount the phase-contrasting elements so that they can be selectively pivoted into the viewing beam paths in order to provide as many possibilities as possible for use of the stereomicroscope of the invention. In this case, the light source diaphragm is advantageously mounted so as to be pivotable into and out of the illuminating beam path.

Figure 6:
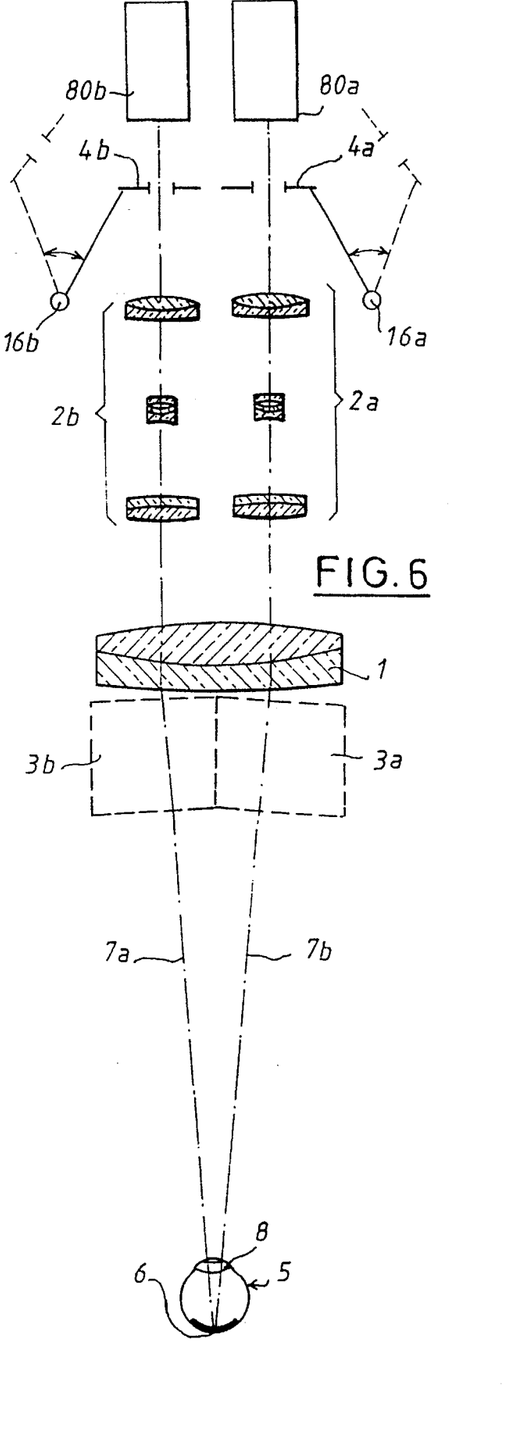
FIG. 6 is a schematic representation of a front elevation view of the stereomicroscope according to another embodiment of the invention showing the phase-contrasting elements pivotally mounted so that they can be pivotally moved into respective ones of the beam paths; and, FIG. 7 is a schematic representation of a front elevation view of a stereomicroscope according to still another embodiment of the invention which includes an intraocular illumination of the eye in lieu of an illumination via the stereomicroscope.

FIG. 6 shows a stereoscopic microscope according to the invention equipped with suitable pivot devices (16a, 16b) for the phase-contrasting elements (4a, 4b). The user in each case can pivot the phase-contrasting elements (4a, 4b) selectively into the stereoscopic viewing beam paths in dependence upon the desired application of the stereomicroscope.

Figure 3A:
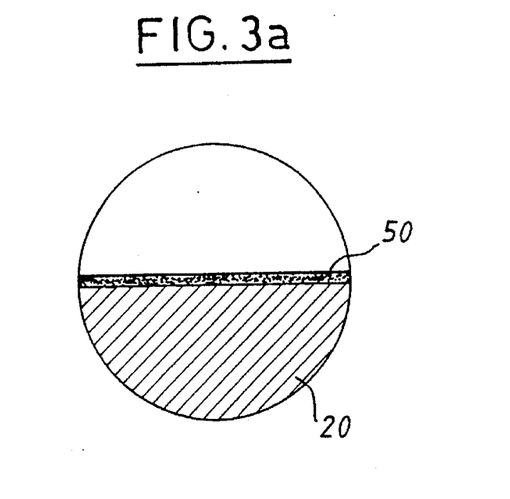
FIGS. 3a to 3c show respectively different possible embodiments of the phase-contrasting elements for a slit-shaped primary light source image.
Figure 3B:
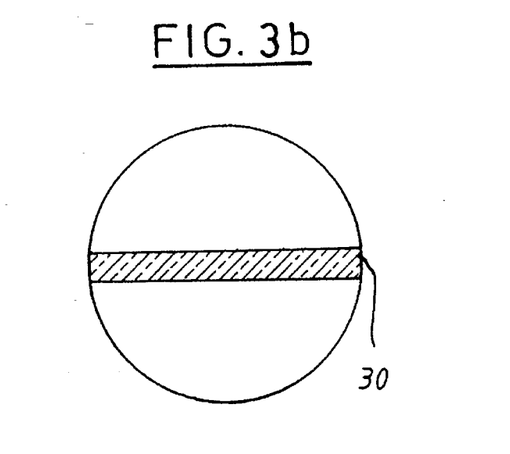
Figure 3C:
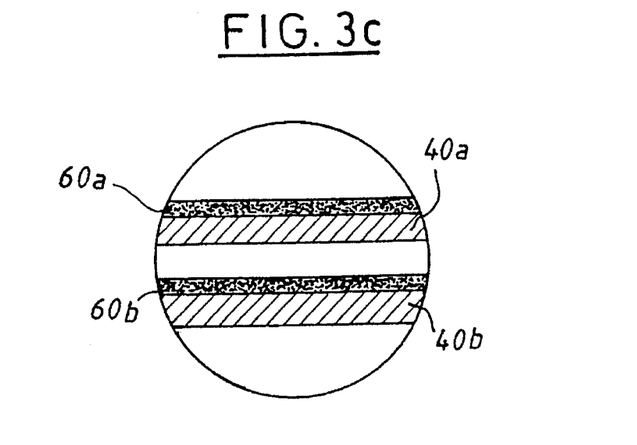

Various embodiments of the phase-contrasting elements are suggested in FIGS. 3a to 3c. These elements are arranged in the secondary light source image plane. Each of FIGS. 3a to 3c show a cross section through a viewing beam path in the secondary light source image plane.

The embodiments shown in FIGS. 3a and 3b are for an illuminating beam path which supplies a line-shaped or rectangular-shaped light source image in the primary light source image plane, that is, on the ocular fundus. Such a line-shaped primary light source image on the ocular fundus is advantageous for ophthalmologic surgery in that the load on the retina caused by the incident radiation intensity is less intense when compared to a point-shaped light source image. The diffraction pattern resulting in the secondary light source image plane is likewise line-shaped or slit-shaped and is likewise orientated as the light source image to the viewing beam paths when a line-shaped or slit-shaped light source image is selected. The higher diffraction orders in this case lie axially symmetrical to the zero diffraction order.

A first possibility for making the transparent phase objects visible (for example, in ophthalmologic surgery) comprises masking out higher diffraction orders in this plane monolaterally or asymmetrically. The remaining wave components which are permitted to pass through in the direction of the viewer interfere and supply an adequate amplitude contrast. For this purpose, and according to FIG. 3a, a diaphragm or edge 20 is introduced asymmetrically into the secondary light source image plane in the viewing beam path and corresponding higher diffraction orders (for example, the +1 order) are asymmetrically masked out.

The line-shaped primary light source image 50 on the ocular fundus is partially visible in FIG. 3a.

A further embodiment for a phase-contrasting element comprises, according to FIG. 3b, a phase plate 30 which definitively shifts the phase of one of the diffraction orders. The phase plate 30 likewise has the form of a narrow rectangle for the selected primary light source image of this embodiment and is arranged in the viewing beam path in the ocular fundus image plane or secondary light source image plane in such a manner that the longitudinal axis of the phase plate 30 is coincident with the symmetry axis of the resulting diffraction pattern. In this way, the phase of the zero diffraction order (that is, of the undiffracted transmitted wave component) is shifted by 90° so that interference results between the transmitted diffraction orders which are now partially changed in phase. The interference of all diffraction orders supplies the required amplitude contrast for the viewer.

In the embodiment of FIG. 3b, a λ/4-plate is mounted as phase plate 30 in the viewing beam path. The λ/4-plate shifts the phase of the zero order by 90°. To increase contrast, the phase plate 30 can be provided with an absorbing layer. In this way, the zero diffraction order is attenuated in its intensity and is matched to the intensity of the higher diffraction orders from which a still further improved amplitude contrast results.

According to the invention, it is further possible to generate several primary light source images on the ocular fundus via a suitable light source diaphragm in order to reduce the load on the ocular fundus caused by the incident light intensity. A reduction of the illuminating intensity on the ocular fundus region charged by the light source then results for a nonetheless adequate overall intensity of the illumination. For this purpose, a multiple diaphragm or a grating can be arranged in the illuminating beam path as a light source diaphragm so that then correspondingly several slit-shaped primary light beam images result on the ocular fundus. To make the media of the forward section of the eye visible as phase objects, the phase-contrasting elements must then likewise be configured as multiple diaphragms or gratings. The phase-contrasting elements can then be selected for each of the slit-shaped light source images as edges of phase plates in the same manner as in the variations already described.

An embodiment for this purpose is shown in FIG. 3c where the phase-contrasting elements (40a, 40b) in the case of two slit-shaped primary beam sources (60a, 60b) are configured as two corresponding grating struts mounted in the viewing beam paths. The grating struts each asymmetrically mask higher diffraction orders. Likewise, the two primary slit-shaped light source images (60a, 60b) can partially be seen on the ocular fundus in FIG. 3c.

The grating constant of the selected light source diaphragm is advantageously so selected that the resulting diffraction orders of the particular secondary light source images do not mutually superpose. Accordingly, a defined intervention in the secondary light source image plane is possible in order to generate the desired interference between higher diffraction orders and undiffracted wave components in each resulting diffraction pattern.

Figure 4A:
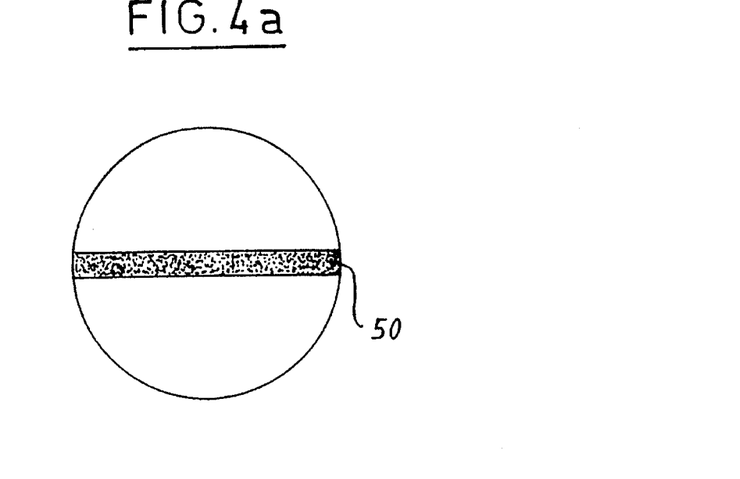
FIG. 4a shows a rectangular-shaped or line-shaped region on the ocular fundus which is provided as a primary light source image.
Figure 4B:
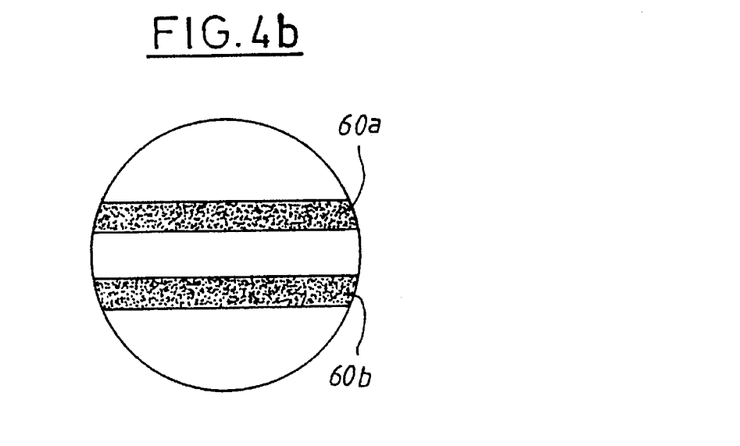
FIG. 4b shows a primary double slit light source image on the ocular fundus.
Figure 4C:
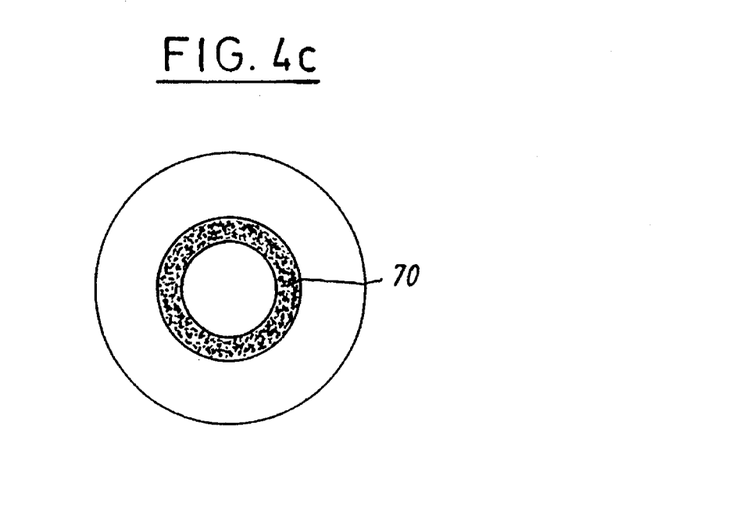
FIG. 4c shows a primary circular ring-shaped light source image on the ocular fundus.

Suitable light source images on the ocular fundus of the eye being viewed are shown in FIGS. 4a to 4c. As already indicated, also the form of the phase contrast element is dependent upon the selection of the primary light source image or the corresponding dimensioning of the illuminating beam path by means of the light source diaphragm. Depending upon the symmetry of the light source image on the ocular fundus, a diffraction image in the secondary light source image plane or ocular fundus image plane results which has a defined symmetry. The particular phase-contrasting element is then to be selected in correspondence to this symmetry.

The desired primary light source image on the ocular fundus is generated by suitable elements in the illuminating beam path such as light source diaphragms and the like.

A possibility for the automated coupling of the primary light source image and the adapted phase-contrasting element as well as the optional selection of various light image sources can be realized by defined switchable diaphragms in the illuminating beam path and correspondingly switchable diaphragms as phase-contrasting elements. Diaphragms of this kind can be configured in an advantageous embodiment as known electrically switchable liquid crystal diaphragms. The use of liquid-crystal elements within a stereomicroscope for various diaphragm types is discussed in U.S. Pat. No. 4,806,776 incorporated herein by reference.

In FIG. 4a, a rectangular-shaped or line-shaped region on the ocular fundus is provided as a primary light source image 50. This region is realized with a corresponding rectangular-shaped or line-shaped light source diaphragm in the illuminating beam path. The embodiments of FIGS. 3a and 3b are suitable for a light source image 50 of this kind.

In FIG. 4b, the already-mentioned primary double slit light source image (60a, 60b) on the ocular fundus is shown. The reduction of the illuminating intensity on the charged region on the ocular fundus is possible with this primary double-slit light source image. For this purpose, suitable phase-contrasting elements are suggested in FIG. 3c.

Furthermore, a circular ring-shaped light source image 70 according to the invention can be utilized on the ocular fundus as shown in FIG. 4c. In the extreme case, this primary circular ring-shaped light source image 70 is distorted into a point-shaped light source image. As indicated above, rotational symmetrical phase-contrasting elements in the viewing beam paths are necessary for this rotational-symmetrical primary light source image 70.

Figure 7:
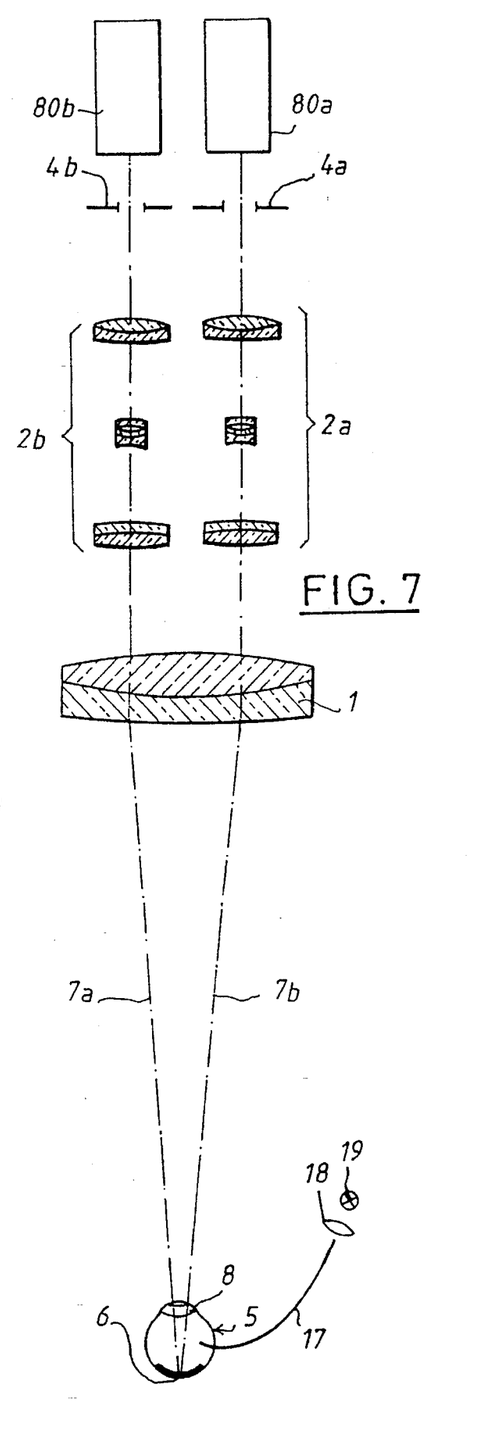

Still another embodiment of the stereoscopic microscope according to the invention is shown in FIG. 7. Here, the transparent forward section of the eye is illuminated via a fiber-optical light conductor 17. The radiation of the desired light source 19 is coupled into the light conductor 17 via a suitable focusing optic 18. A transillumination of the transparent portion of the forward section of the eye is here provided from the rear thereof.

It is understood that the foregoing description is that of the preferred embodiments of the invention and that various changes and modifications may be made thereto without departing from the spirit and scope of the invention as defined in the appended claims.

What is claimed is:

1. A stereomicroscope, especially of the kind utilized to conduct ophthalmologic surgery, for making transparent media visible, the stereomicroscope comprising:

first and second optics defining first and second viewing beam paths;

said transparent media defining objects, said objects being phase objects in transilluminating light and being positioned in said beam paths;

a light source arrangement for imaging illuminating light into a primary light source image on a light-reflecting surface, said primary light source image being reflected by said light-reflecting surface to produce wave components of reflected light transmitted through said objects and along said viewing beam paths whereby said objects form diffraction images and effect phase shifts of the diffracted wave components of said reflected light corresponding to said diffraction images;

said light-reflecting surface defining a first image plane and said first and second optics being configured to image said primary light source image including said diffraction images in a second image plane on said viewing beam paths; and, phase contrasting elements disposed in said beam paths, respectively, for translating said phase shifts into amplitude contrasts visible to a person viewing with said stereomicroscope.

2. The stereomicroscope of claim 1, said light source arrangement including elements for imparting a predetermined form and size to said image; and, said light-source arrangement further comprising a deflecting element for deflecting said illuminating light into said first and second beam paths and onto said light-reflecting surface at which the light of said primary light source image is reflected back along said beam paths to transilluminate said phase objects.

3. The stereomicroscope of claim 2, said phase contrasting elements being mounted at or near said second image plane.

4. The stereomicroscope of claim 3, said first and second optics including first and second binocular tubes and first and second magnification changing optical devices arranged along said first and second beam paths, respectively; and, said second image plane being disposed on said beam paths between said binocular tubes and said magnification changing optical devices.

5. The stereomicroscope of claim 3, said light source arrangement comprising: a light source for providing said illuminating light; and, said elements for imparting a predetermined form and size to said primary light source image being at least one diaphragm mounted in said illuminating light for dimensioning the form and size of said primary light source image in said first image plane.

6. The stereomicroscope of claim 5, said diaphragm being configured to have at least one slit.

7. The stereomicroscope of claim 5, said diaphragm being configured to generate a rotationally symmetrical primary light source image.

8. A stereomicroscope, especially of the kind utilized to conduct ophthalmologic surgery, for making transparent media visible, the stereomicroscope comprising:

first and second optics defining first and second viewing beam paths;

said transparent media defining objects, said objects being phase objects in transilluminating light and being positioned in said beam paths;

a light source arrangement for imaging illuminating light into a primary light source image on a light-reflecting surface, said primary light source image being reflected by said light-reflecting surface to produce wave components of reflected light transmitted through said objects and along said viewing beam paths whereby said objects form diffraction images and effect phase shifts of the diffracted wave components of said reflected light corresponding to said diffraction images;

said light-reflecting surface defining a first image plane and said first and second optics being configured to image said primary light source image including said diffraction images in a second image plane on said viewing beam paths;

phase contrasting elements disposed in said beam paths, respectively, for translating said phase shifts into amplitude contrasts visible to a person viewing with said stereomicroscope;

said light source arrangement including elements for imparting a predetermined form and size to said image; and, said light-source arrangement further comprising a deflecting element for deflecting said illuminating light into said first and second beam paths and onto said light-reflecting surface at which the light of said primary light source image is reflected back along said beam paths to transilluminate said phase objects;

said phase contrasting elements being mounted at or near said second image plane;

said first and second optics including first and second binocular tubes and first and second magnification changing optical devices arranged along said first and second beam paths, respectively; and, said second image plane being disposed on said beam paths between said binocular tubes and said magnification changing optical devices; and, a coupling unit for coupling the position of said phase contrasting elements and the magnification of said first and second magnification changing optical devices whereby said phase contrasting elements are always positioned in said second image plane for every possible selected magnification.

9. The stereomicroscope of claim 8, said phase contrasting elements comprising first and second phase contrasting elements arranged in said first and second beam paths, respectively; and, each of said phase contrasting elements comprising at least one plate which shifts the phase of one of said diffracted wave components in said second image plane in a defined manner.

10. The stereomicroscope of claim 9, said phase contrasting elements comprising first and second phase contrasting elements arranged in said first and second beam paths, respectively; and, each of said phase contrasting elements comprising a phase plate defining a grating.

11. The stereomicroscope of claim 8, said phase contrasting elements comprising first and second phase contrasting elements arranged in said first and second beam paths, respectively; and, each of said phase contrasting elements comprising a diaphragm defining an edge for asymmetrically masking out at least one of said diffracted wave components in said second image plane.

12. The stereomicroscope of claim 11, said phase contrasting elements comprising first and second phase contrasting elements arranged in said first and second beam paths, respectively; and, each of said phase contrasting elements comprising a diaphragm defining a plurality of edges.

13. A stereomicroscope, especially of the kind utilized to conduct ophthalmologic surgery, for making transparent media visible, the stereomicroscope comprising:

first and second optics defining first and second viewing beam paths;

said transparent media defining objects, said objects being phase objects in transilluminating light and being positioned in said beam paths;

a light source arrangement for imaging illuminating light into a primary light source image on a light-reflecting surface, said primary light source image being reflected by said light-reflecting surface to produce wave components of reflected light transmitted through said objects and along said viewing beam paths whereby said objects form diffraction images and effect phase shifts of the diffracted wave components of said reflected light corresponding to said diffraction images;

said light-reflecting surface defining a first image plane and said first and second optics being configured to image said primary light source image including said diffraction images in a second image plane on said viewing beam paths;

phase contrasting elements disposed in said beam paths, respectively, for translating said phase shifts into amplitude contrasts visible to a person viewing with said stereomicroscope;

said light source arrangement including elements for imparting a predetermined form and size to said image; and, said light-source arrangement further comprising a deflecting element for deflecting said illuminating light into said first and second beam paths and onto said light-reflecting surface at which the light of said primary light source image is reflected back along said beam paths to transilluminate said phase objects;

said phase contrasting elements being mounted at or near said second image plane;

said light source arrangement comprising: a light source for providing said illuminating light; and, said elements for imparting a predetermined form and size to said primary light source image being at least one diaphragm mounted in said illuminating light for dimensioning the form and size of said primary light source image in said first image plane; and, said phase contrasting elements comprising a first plurality of phase contrasting elements corresponding to said first beam path and a second plurality of phase contrasting elements corresponding to said second beam paths; and, a switching device for selectively switching at least one of said first plurality of phase contrasting elements into said first beam path and for selectively switching at least one of said second plurality of phase contrasting elements into said second beam path.

14. A stereomicroscope for conducting surgery on the eye which includes an ocular fundus and a forward section containing a transparent media in the form of lens residues, the stereomicroscope comprising:

first and second optics defining first and second viewing beam paths;

said transparent media defining objects, said objects being phase objects and being positioned in said beam paths;

a light source arrangement for imaging illuminating light into a primary light source image at the ocular fundus, said primary light source image being reflected by said ocular fundus to produce wave components of reflected light transmitted through said objects and along said viewing beam paths whereby said objects form diffraction images and effect phase shifts of the diffracted wave components of said reflected light corresponding to said diffraction images;

said ocular fundus defining a first image plane and said first and second optics and the eye conjointly imaging said primary light source image including said diffraction images in a second image plane on said viewing beam paths; and, phase contrasting elements mounted in said beam paths, respectively, for translating said phase shifts into amplitude contrasts visible to a person viewing with said stereomicroscope.

15. A method for providing an improved contrast of transparent media with a stereomicroscope, especially of the kind utilized to conduct ophthalmologic surgery, the transparent media defining phase objects in transilluminating light, the stereomicroscope including first and second optics defining first and second viewing beam paths, the method comprising the steps of:

positioning said transparent media in said beam paths;

providing a light source device for imaging illuminating light into a primary light source image at a light-reflecting surface defining a first image plane, said primary light source image being reflected by said light-reflecting surface to produce wave components of reflected light transmitted through said transparent media and along said viewing beam paths whereby said phase objects form diffraction images and effect phase shifts of the diffracted wave components of said reflected light corresponding to said diffraction images;

utilizing said first and second optics to image said primary light source image including said diffraction images in a second image plane on said viewing beam paths; and, introducing phase contrasting elements into said beam paths, respectively, for translating said phase shifts into amplitude contrasts visible to a person viewing with said stereomicroscope.

16. The method of claim 15, wherein said light source device includes a light source and a diaphragm for imparting a predetermined form and size to said primary light source image; and, wherein the method comprises the further step of selecting said phase contrasting elements in said second image plane in correspondence to said predetermined form and size of said primary light source image.

17. The method of claim 16, wherein said light-reflecting surface is the ocular fundus of the eye and said transparent media are transparent parts of the eye which are made visible by said amplitude contrasts.

18. A method for contrasting transparent media in the human eye, the transparent media defining phase objects in light transmitted therethrough, the method comprising the steps of:

providing a stereomicroscope having first and second optics defining first and second viewing beam paths;

positioning the transparent media;

intraocularly placing a light source in the eye and transilluminating the transparent media with wave components of transilluminating light which travel along said viewing beam paths whereby said phase objects form diffractive images and effect phase shifts of the diffracted wave components of said transilluminating light corresponding to said diffraction images;

utilizing the eye and said first and second optics to image said diffraction images in an image plane on said beam paths; and, introducing phase contrasting elements in said image plane in corresponding ones of said beam paths thereby translating said phase shifts into amplitude contrasts visible to a person viewing with said stereomicroscope.

* * * * *